United States Patent [19]
Endo et al.

[11] Patent Number: 5,452,337
[45] Date of Patent: Sep. 19, 1995

[54] RADIATION DIAGNOSTIC SYSTEM

[75] Inventors: Masahiro Endo; Yukio Tateno, both of Chiba; Masao Jinbo, Tochigi; Masahiro Kusakabe, Kanagawa; Kazumasa Sato, Tokyo; Tsutomu Okazaki, Kanagawa, all of Japan

[73] Assignees: Sony Corporation; National Institute of Radiological Science, Science and Technology Agency, Japan

[21] Appl. No.: 150,177
[22] PCT Filed: Mar. 3, 1993
[86] PCT No.: PCT/JP93/00272
§ 371 Date: Nov. 30, 1993
§ 102(e) Date: Nov. 30, 1993
[87] PCT Pub. No.: WO93/19672
PCT Pub. Date: Oct. 14, 1993

[30] Foreign Application Priority Data

Apr. 1, 1992 [JP] Japan .................................. 4-105282

[51] Int. Cl.⁶ .................................................. A61B 6/00
[52] U.S. Cl. .................................. 378/4; 378/11; 378/19
[58] Field of Search ................... 378/4, 13, 11, 15, 19, 378/22, 62

[56] References Cited

U.S. PATENT DOCUMENTS

| | | | |
|---|---|---|---|
| 4,035,651 | 7/1977 | LeMay | 378/19 X |
| 4,138,610 | 2/1979 | Weinkauf | 378/19 |
| 4,149,080 | 4/1979 | Schittenhelm | 378/19 X |
| 4,204,124 | 5/1980 | Kowalski | 378/9 |
| 4,260,895 | 4/1981 | Schittenhelm | 378/19 X |
| 4,309,615 | 1/1982 | Kowalski | 378/4 X |
| 4,873,708 | 10/1989 | Cusano et al. | 378/19 X |
| 5,073,910 | 12/1991 | Eberhard et al. | 378/4 |
| 5,138,642 | 8/1992 | McCroskey et al. | 378/19 |
| 5,241,576 | 8/1993 | Lonn | 378/19 |
| 5,253,171 | 10/1993 | Hsiao et al. | 378/4 X |
| 5,323,439 | 6/1994 | Nobuta et al. | 378/4 X |

FOREIGN PATENT DOCUMENTS

| | | | |
|---|---|---|---|
| 54-13786 | 2/1979 | Japan | A61B 6/02 |
| 55-45413 | 3/1980 | Japan | A61B 6/02 |
| 62-87138 | 4/1987 | Japan | A61B 6/03 |
| 63-2607 | 1/1988 | Japan | A61B 6/03 |
| 3-109054 | 11/1991 | Japan | G01N 27/403 |

*Primary Examiner*—David P. Porta
*Attorney, Agent, or Firm*—Limbach & Limbach; W. Patrick Bengsston

[57] ABSTRACT

A rotational drive sensor 31 which allows a radiation source 10 and a two-dimensional sensor 20 which are caused to be in one body to turn round a subject 50. An X-ray vessel 13 irradiates X-rays to the subject 50 in a pulsated manner. An X-ray/light conversion element 21 converts an X-ray transmitted image to an optical image. A CCD camera 23 picks up this optical image. An information processing unit 40 reconstructs a three-dimensional pictorial image on the basis of two dimensional pictorial images in plural directions obtained, and a display monitor 46 displays this three-dimensional pictorial image. A controller 39 controls the distance between the X-ray vessel 13 and the X-ray/light conversion element 21 and the focal size of the X-ray vessel 13 on the basis of the size of the subject 50. As a result, it is possible to obtain, in a short time, a three-dimensional pictorial image having less distortion and high resolution in a broad region, and to reduce X-ray exposure quantity to much more degree as compared to the conventional system.

7 Claims, 2 Drawing Sheets

RADIATION DIAGNOSTIC SYSTEM

TECHNICAL FIELD

This invention relates to a radiation diagnostic system, and more particularly to a radiation diagnostic system capable of providing a three-dimensional pictorial image.

BACKGROUND ART

Radiation diagnostic system, also known as X-ray television system, X-ray CT (Computer Tomography) system, etc., are known prior art.

The conventional X-ray television system converts an X-ray transmitted image obtained by irradiating X-rays onto a subject to a bright optical image by means of an X-ray image intensifier that picks up this optical image by means of a video camera. Accordingly, with such an X-ray television system, a two-dimensional pictorial image could be obtained, but a three-dimensional pictorial image (images of many layers or layered surfaces) cannot be obtained. In this case, the X-ray image intensifier has a dimension of 14 inches (diameter of about 35 cm) even at the maximum. For this reason, a large visual field cannot be provided. For example, it was impossible to cover the entirety of the breast. In addition, there was also the problem that the image distortion is large because such an intensifier is apt to be affected by vibration or geomagnetism.

On the other hand, the conventional X-ray CT system is adapted to allow an X-ray source and one-dimensional array sensor which are caused to be in one body to turn round a subject to form an image of each layer from one-dimensional transmitted images in plural directions obtained from the one-dimensional array sensor, e.g., by the so-called convolution back projection method (Reference Literature: L. A. Feldkamp, L. C. Davis, and J. W. Kress, "Practical cone-beam algorithm", J. Opt. Soc. Am. A/Vol. 1, No. 6 612–619/June 1984), or the Fast Fourier Transform (FFT) method. Accordingly, with such an X-ray CT system, only images of two or three layers, for example, could be obtained at best every one rotation. In order to obtain images of many layers, e.g., images of 128 layers, when it is assumed to take five seconds per each layer, it would take 640 ($=5 \times 128$) seconds. Accordingly, such X-ray CT system is insufficient as a clinical system for patients, and there was also the problem that a quantity of X-ray exposure becomes vast. In other words, when a quantity of exposure is taken into consideration, the resolution in a body axis direction connecting the head and the foot of a patient could not be so much high.

As stated above, in the conventional X-ray television system, there is the problem that a three-dimensional pictorial image cannot be provided, or the like. On the other hand, in the conventional X-ray CT system, a three-dimensional pictorial image can be obtained, but there were the problems that it takes much time, a quantity of X-ray exposure is large, the resolution in a body axis direction is poor, and the like.

This invention has been made in view of such actual circumstances, and its object is to provide a radiation diagnostic system capable of obtaining, in a short time, a three-dimensional pictorial image having less distortion and a high resolution in a broad region.

DISCLOSURE OF THE INVENTION

A first radiation diagnostic system according to this invention is characterized by the provision of a radiation output means for outputting radioactive rays, a two-dimensional radiation detecting means disposed at the position opposite to the radiation output means through a subject and adapted to detect the intensity distribution of radioactive rays transmitted through the subject, a rotation drive means for allowing the radiation output means and the two-dimensional radiation detecting means which are caused to be in one body to turn round the subject, and an information processing means for forming a three-dimensional pictorial image on the basis of the intensity distribution of radioactive rays in plural directions from the two-dimensional radiation detecting means.

A second radiation diagnostic system according to this invention is characterized in that in the first radiation diagnostic system, the radiation output means is comprised of an X-ray source, and the two-dimensional radiation detecting means is composed of an X-ray/light conversion element for converting X-rays to (rays of) a visible light and a CCD camera.

A third radiation diagnostic system according to this invention is characterized in that in the second radiation diagnostic system, the X-ray/light conversion element is comprised of a fluorescent substance including rare earth element.

A fourth radiation diagnostic system according to this invention is characterized in that in the first radiation diagnostic system, there is provided a drive means for allowing the distance between the radiation output means and the two-dimensional radiation detecting means to be adjustable.

A fifth radiation diagnostic system according to this invention is characterized in that in the fourth radiation diagnostic system, there are provided display means for displaying a pictorial image based on the intensity distribution of radioactive rays from the two-dimensional radiation detecting means, and control means for determining a distance between the radiation output means and the two-dimensional radiation detecting means such that the ratio of an image of the subject occupied on the screen takes a value more than a predetermined value, on the basis of a profile (contour) of the image of the subject displayed on the display means, and for controlling the drive means so that the distance is provided.

A sixth radiation diagnostic system according to this invention is characterized in that in the fourth or fifth radiation diagnostic system, the radiation output means is comprised of an X-ray source having at least two focal sizes, and the system further includes a switching means for switching and selecting the focal size in dependency upon the distance between the radiation output means and the two-dimensional radiation detecting means.

A seventh radiation diagnostic system according to this invention is characterized in that in the first radiation diagnostic system, the two-dimensional radiation detecting means includes a picture angle adjustment means for adjusting a picture angle.

An eighth radiation diagnostic system according to this invention is characterized in that in the seventh radiation diagnostic system, the radiation output means is comprised of an X-ray source, and the two-dimensional radiation detecting means is composed of an X-ray/light conversion element for converting X-rays to (rays of) a visible light and a CCD camera provided with a zoom lens as the picture angle adjustment means.

A ninth radiation diagnostic system according to this invention is characterized in that in the seventh radiation diagnostic system, the radiation output means is comprised of an X-ray source, and the two-dimensional radiation detecting means is composed of an X-ray/-light conversion element for converting X-rays to (rays of) a visible light and a CCD camera, the system further including, as the picture angle adjustment means, a moving means for moving the CCD camera in an optical axis direction thereof.

A tenth radiation diagnostic system according to this invention is characterized in that in the first radiation diagnostic system, there are provided a bed for mounting a patient as the subject thereon and a bed drive means for moving the bed in a body axis direction of the patient.

An eleventh radiation diagnostic system according to this invention is characterized in that in the tenth radiation diagnostic system, there are provided a display means for displaying a pictorial image based on the intensity distribution of radioactive rays from the two-dimensional radiation detecting means, and control means for controlling the bed drive means so that an interest region is located substantially at the central portion of the screen of the display means, on the basis of a profile (contour) of an image of the subject displayed on the display means.

A twelfth radiation diagnostic system according to this invention is characterized in that in the first radiation diagnostic system, the information processing means forms a three-dimensional pictorial image by the convolution back projection method.

A thirteenth radiation diagnostic system according to this invention is characterized in that in the twelfth radiation diagnostic system, the information processing means forms a two-dimensional pictorial image in a body axis direction or in a direction perpendicular to the body axis direction of the patient as the subject.

BEST MODE FOR CARRYING OUT THE INVENTION

A preferred embodiment of a radiation diagnostic system according to this invention will now be described with reference to the attached drawings.

Figure 1:
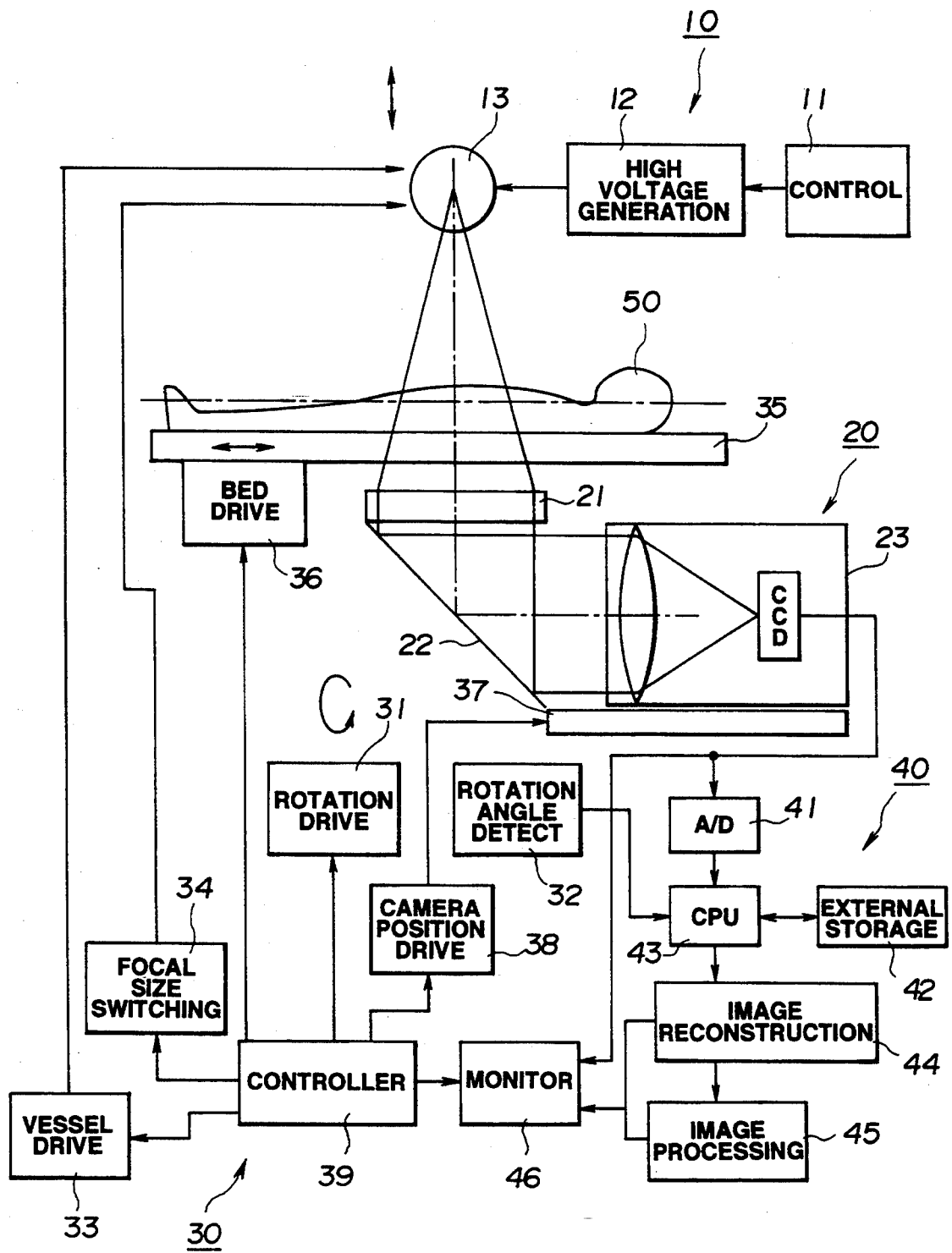
FIG. 1 is a block diagram showing an actual configuration of a radiation diagnostic system to which this invention is applied.

A radiation diagnostic system to which this invention is applied comprises, as shown in FIG. 1, for example, a radiation source 10 for outputting radioactive rays, a two-dimensional sensor 20 disposed at the position opposite to the radiation source 10 through a subject 50 and adapted to detect the intensity distribution of radioactive rays transmitted through the subject 50, a drive unit 30 adapted to allow the radiation source 10 and the two-dimensional sensor 20 which are caused to be in one body to turn round the subject 50, and/or to vary the distance between the radiation source 10 and the two-dimensional sensor 20, or the like, and an information processing unit 40 for forming a three-dimensional pictorial image on the basis of the intensity distribution of radioactive rays in plural directions from the two-dimensional sensor 20.

More particularly, the radiation source 10 comprises, as shown in the above-mentioned FIG. 1, a control section 11, a high voltage generator 12 for generating a high voltage under control of the control section 11, and an X-ray vessel 13 for outputting radioactive rays, e.g., X-rays by the high voltage from the high voltage generator 12. This X-ray vessel 13 has at least two so-called focal sizes so that a desired one thereof can be selected.

Further, the two-dimensional sensor 20 comprises, similarly as shown in FIG. 1, an X-ray/light conversion element 21 for converting X-rays transmitted through the subject 50 to (rays of) a visible light a mirror 22 for allowing the traveling direction of the visible light from the X-ray/light conversion element 21 to be in correspondence with a direction perpendicular thereto, and a CCD video camera (hereinafter simply referred to as a CCD camera) 23 for picking up an optical image formed by the X-ray/light conversion element 21.

In addition, the drive unit 30 comprises, similarly as shown in FIG. 1, a rotation drive section 31 for allowing the radiation source 10 and the two-dimensional sensor 20 which are caused to be in one body to turn round the subject 50, a rotation angle detector 32 for detecting a rotational angle provided by rotation by the rotation drive section 31, a vessel drive section 33 for allowing the distance between the X-ray vessel 13 and the X-ray/light conversion element 21 to be adjustable, a focal size switcher 34 for switching and selecting the focal size of the X-ray vessel 13, a bed 35 for mounting a patient as the subject 50 thereon, a bed drive section 36 for moving the bed 35 in a body axis direction of the patient a camera mount 37 adapted so that the CCD camera 23 is mounted thereon and it is moved in the optical axis direction of the camera, a camera position drive section 38 for moving the camera mount 37 in the optical axis direction of a visible light reflected by the mirror 22, and a controller 39 for controlling the components mentioned above.

In this radiation diagnostic system, a scheme is employed to convert an X-ray transmitted image obtained by irradiating X-rays from the X-ray vessel 13 onto the subject 50 to an image of a visible light (optical image) by means of the X-ray/light conversion element 21 to pick up that optical image by using the CCD camera 23, and to repeat the above-mentioned operation every predetermined rotational angle, i.e., at a predetermined period while allowing the radiation source 10 and the two-dimensional sensor 20 which are caused to be in one body to turn round the subject 50, thus to form a three-dimensional pictorial image on the basis of two-dimensional pictorial images in plural directions obtained.

In actual terms, the control section 11 controls the high voltage generator 12 so as to apply a predetermined valve voltage and a predetermined valve current to the X-ray vessel 13 for a short time period and at a predetermined period (which will be referred to as "in a pulsated manner"). For example, the control section 11 controls the high voltage generator 12 so that the number of irradiations of X-rays is more than 120 for a time period during which the X-ray vessel 13 and the two-dimensional sensor 20 rotate in such a manner that they are caused to be in one body at 180+α degrees (α is so called a fan angle and this rotation is simply referred to as half turn of the X-ray vessel 13) on the surface perpendicular to the body axis connecting the head and the foot of the patient as the subject 50. Thus, X-rays from the X-ray vessel 13 are transmitted through the subject 50 mounted on the bed 35. As a result X-rays having an intensity distribution based on differences of the X-ray absorption coefficients $\mu$ of the interior of the subject 50 are incident to the X-ray/light conversion element 21. It is to be noted that the rotational angle of the X-ray vessel 13 may be one rotation (360+$\alpha$ degrees).

The X-ray/light conversion element 21 is comprised of fluorescent substance including rare earth element having an excellent X-ray stopping power, e.g., $Gd_2O_2S$:Tb, $Gd_2O_2S$:Eu, etc., and takes a form, e.g., a plane surface such that it can cover the entirety of the breast. This X-ray/light conversion element 21 serves to convert X-rays to (rays of) a visible light. The traveling direction of the visible light from the X-ray/light conversion element 21 is changed so that it is in correspondence with a direction perpendicular thereto. The visible light thus obtained from the mirror 22 is incident to the CCD camera 23, at which picking up of an optical image is carried out. A video signal based on the picked up image from the CCD camera 23 is delivered to the information processing unit 40. Meanwhile, as described above, a fluorescent substance including rare earth element having X-ray excellent stopping power is used as the X-ray/light conversion element 21. Further, the traveling direction of the visible light is changed by the mirror 22 so that X-rays which have not been converted by the X-ray/light conversion element 21 are not irradiated to the CCD camera 23. Thus, it is possible to prevent in advance failure of the CCD camera 23 due to the X-ray. It is to be noted that e.g., a video camera using so called an image pickup tube may be used in place of such CCD camera.

The information processing unit 40 comprises, as shown in the above-mentioned FIG. 1, for example, an A/D converter 41 for converting a video signal from the CCD camera 23 to a digital video signal; an external storage section 42 for storing the digital video signal from the A/D converter 41; a Central Processing Unit (hereinafter referred to as a CPU) 43 for controlling inputs of the digital video signal from the A/D converter 11, or the like; an image reconstruction section 44 for implementing pre-processing such as luminance correction, etc. to the digital video signal which has been read out from the external storage section 42, and for forming a three-dimensional pictorial image on the basis of the pre-processed digital video signal, i.e., two-dimensional pictorial images in plural directions; an image processing section 45 for implementing image processing such as extraction of contour, etc. to the three-dimensional pictorial image from the image reconstruction section 44 as occasion demands; and a display monitor 46 for displaying a pictorial image based on three-dimensional image data from the image processing section 45, and adapted so that position, etc. on the screen can be designated.

The A/D converter 41 converts a video signal, e.g., a luminance signal from the CCD camera 23 to a digital video signal. The luminance data in a digital form thus obtained is stored into the external storage section 42 under control of the CPU 43. In actual terms, the rotation angle detector 32 detects a rotational angle when the radiation source 10 and the two-dimensional sensor 20 turn round the subject 50 in such a manner that they are in one body. The CPU 43 carries out a control so as to collect luminance data in synchronism with a pulsated, or pulse like irradiation of the above-described X-ray vessel 13 to store the collected luminance data into the external storage section 42. Namely, X-rays irradiated onto the subject 50 are caused to have a pulse like form, thereby making it possible to prevent useless exposure to the subject 50 to much more degree as compared to the case where they are continuously irradiated. In such pulsated X-ray irradiation, for example, since the irradiation time is short the irradiation intensity of X-ray can be enhanced. As a result, so called a S/N (Signal to Noise ratio) can be improved. It is to be noted that e.g., luminance data may be stored into the internal memory of the information processing unit 40 in place of storing such data into the external storage section 42.

In a manner as stated above, luminance data in plural directions (e.g., more than 120 directions) stored in the external storage section 42 are read out for a second time under control of the CPU 43, and are then delivered to the image reconstruction section 44.

The image reconstruction section 44 implements, to the luminance data which has been read out pre-processing such as geometrical distortion correction for correcting a geometrical distortion, luminance correction, conversion for converting luminance data into X-ray absorption data, etc. to form images of plural layered surfaces (three-dimensional pictorial image data) by, e.g., the so-called convolution back projection method or the Fast Fourier Transform (FFT) method by using the X-ray absorption data in plural directions obtained to deliver the three-dimensional pictorial image data to the image processing section 45.

Figure 2:
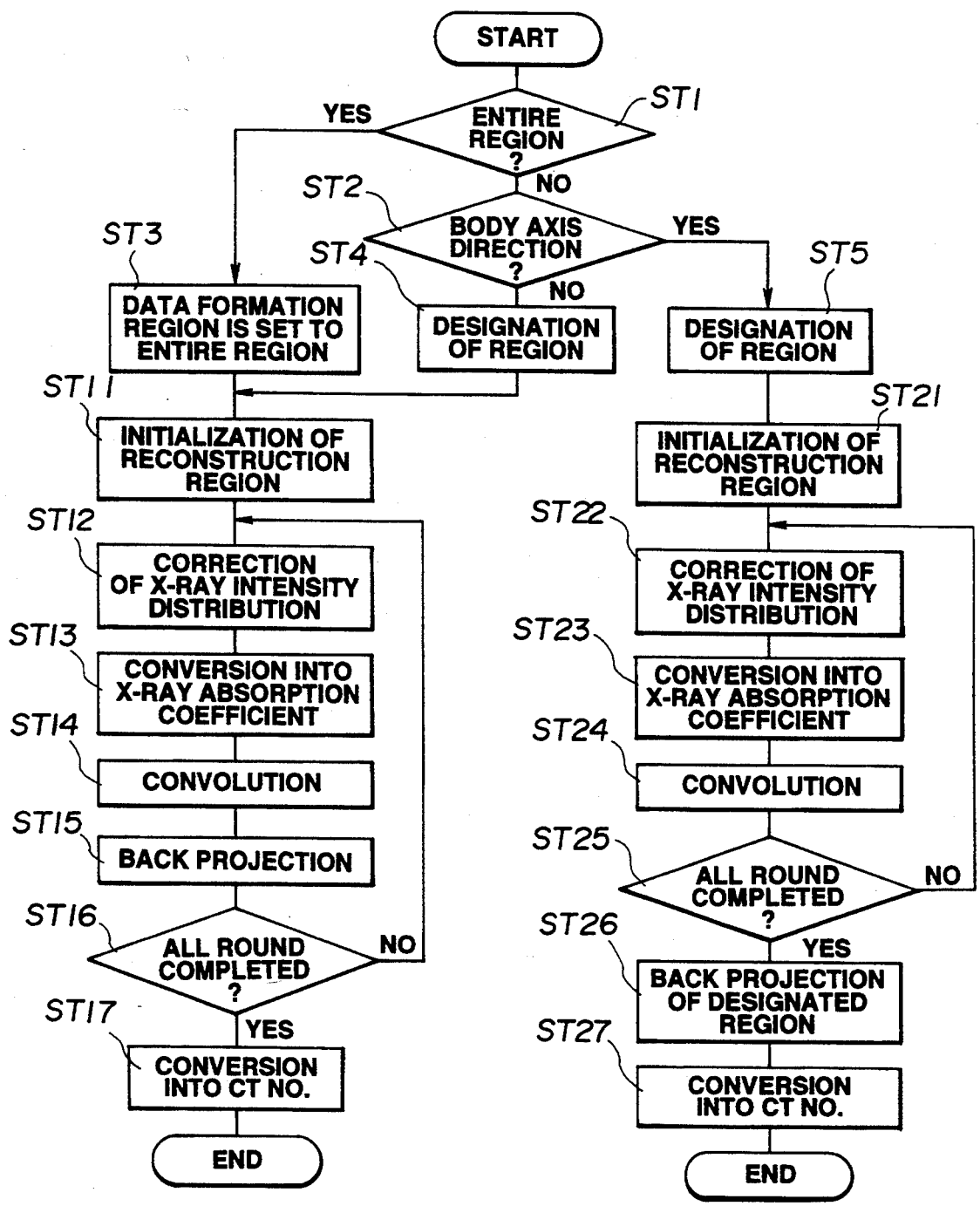
FIG. 2 is a flowchart for explaining an actual operation of an image reconstruction section constituting the radiation diagnostic system.

In actual terms, as shown in FIG. 2, for example, at step ST1, the image reconstruction section 44 judges whether or not an operator carries out an operation so as to form three-dimensional image data over the entire region. As a result when it is judged that the operator carries out such an operation, the operation proceeds to step ST3. In contrast when it is judged that the operator does not carry out such an operation, the operation proceeds to step ST2.

At the step ST2, the image reconstruction section 44 judges whether the layered surface in the region designated at the step ST1 is a layered surface in a body axis direction or a layered surface in a direction perpendicular to the body axis. As a result when it is judged that the layered surface in the designated region is that in the body axis direction, the operation proceeds to step ST5. In contrast when it is judged that the layered surface in the designated region is that in the direction perpendicular to the body axis, the operation proceeds to step ST4.

At the step ST3, the image reconstruction section 44 forms three-dimensional image data in the entire region. The operation then proceeds to step ST11.

At the step ST4, the image reconstruction section 44 forms three-dimensional image data in the designated region. The operation then proceeds to the step ST11.

Further, at step ST5, the image reconstruction section 44 forms three-dimensional image data in the designated region, The operation then proceed to step ST21.

At the step ST11, the image reconstruction section 44 initializes the reconstruction region for storing three-dimensional image data of a memory included therein, e.g., set the value to zero (0). The operation then proceeds to step ST12.

At the step ST12, since the intensity of the X-ray is high at the central portion and is low at the peripheral portion, the image reconstruction section 44 corrects unevenness due to position on the basis of an X-ray intensity distribution measured in advance. Namely, when it is now assumed that, e.g., the maximum luminance distribution and the minimum luminance distribution which have been measured in advance are respectively M (x, y) and B (x, y), and that luminance data at a collected rotational angle d is $i_d(x, y)$, the image reconstruction section 44 determines corrected luminance data $I_d(x, y)$ by the following formula (1). The operation then proceeds to step ST13:

$$I_d(x, y) = (i_d(x, y) - B(x, y))/(M(x, y) - B(x, y)) \quad \text{[Formula (1)]}$$

At the step ST13, because the intensity exponentially lowers when X-rays are passed through the absorber, the image reconstruction section 44 determines absorption coefficients (X-ray absorption data) $P_d(x, y)$ from the corrected luminance data $I_d(x, y)$, e.g., by the following formula (2). The operation then proceeds to step ST14, It is to be noted that H is an arbitrary coefficient and its value is, e.g., 1000:

$$P_d(x, y) = H - (H/\text{Log } H) \times \text{Log } (X \times I_d(x, y)) \quad \text{[Formula 2)]}$$

At the step ST14, the image reconstruction section 44 carries out convolution (superimposing integration) of the X-ray absorption data $P_d(x, y)$ and the correction function (e.g., correction function of Shepp and Logan) to generate projection data. The operation then proceeds to step ST15.

At the step ST15, the image reconstruction section 44 accumulatively stores projection data into the reconstruction region initialized at the step ST11. The operation then proceeds to step ST16.

At the step ST16, the image reconstruction section 44 judges whether or not it has accumulatively stored projection data in all directions. As a result when it is judged that the image reconstruction section 44 has accumulatively stored such projection data, the operation proceeds to step S17. In contrast when it is judged that the image reconstruction section 44 has not done so, the operation returns to the step ST12. Namely, e.g., projection data in respective directions are back-projected at respective pixel positions of the reconstruction region which has, e.g., three-dimensional configuration and are sequentially accumulated thereon. As a result a three-dimensional absorption coefficient pictorial image is formed in the reconstruction region. Meanwhile, when the image reconstruction section 44 executes the processing of this loop through the step ST3, forms an absorption coefficient pictorial image over the entire region. On the other hand, when the image reconstruction section 44 executes the processing of this loop through the step ST4, it forms absorption coefficient images of a single or plural layered surfaces perpendicular to the body axis, for example, over the designated region.

At the step ST17, the image reconstruction section 44 calibrates, by absorption coefficient values of air and water measured in advance, values of respective pixels of absorption coefficient images formed in the reconstruction region to convert them to so called CT number values. Thus, the image reconstruction section 44 forms three-dimensional image data (images of plural layered surfaces) comprised of CT number values. Meanwhile, in order to form three-dimensional image data by the back projection method, many operations are required (it takes much time). This radiation diagnostic system designates a desired region as described above prior to forming three-dimensional pictorial image data in the entire region by the back projection method to form two-dimensional image data (images of layered surfaces perpendicular to the body axis) which are images of a single or plural layered surfaces in the above-mentioned region and are comprised of CT numbers, thus making it possible to display, on the display monitor 46, pictorial images based on the two-dimensional image data as described later. Thus, an operator observes the pictorial images displayed, thus making it possible to confirm in a short time whether collected luminance data is good or bad, e.g., presence or absence of the influence of noise, etc. In other words, it is possible to judge, without unduly delaying a waiting patient, whether or not collection of luminance data is required for a second time, e.g., because of many noises.

On the other hand, at step ST21, the image reconstruction section 44 initializes the reconstruction region. Thus, the operation proceeds to step ST22.

At the step ST22, the image reconstruction section 44 determines corrected luminance data $I_d(x, y)$ by the above-mentioned formula (1). The operation then proceeds to step ST23.

At the step ST23, the image reconstruction section 44 determines X-ray absorption data $P_d(x, y)$ from the corrected luminance data $I_d(x, y)$ by the above-mentioned formula (2). The operation then proceeds to step ST24.

At the step ST24, the image reconstruction section 44 carries out convolution of the X-ray absorption data $P_d(x, y)$ and the correction function to generate projection data. The operation then proceeds to step ST25.

At the step ST25, the image reconstruction section 44 judges whether or not it generates projection data over the entire circumference. As a result when it is judged that the image reconstruction section 44 generates such data, the operation proceeds to step ST26. In contrast when it is judged that the image reconstruction section 44 does not generate such data, the operation returns to the step ST22.

At the step ST26, the image reconstruction section 44 back-projects projection data from respective directions onto respective pixel positions in the region designated by the step ST5 in the reconstruction region to sequentially accumulate them. The operation then proceeds to step ST27. As a result a single or plural two-dimensional absorption coefficient pictorial images in the body axis direction are formed in the reconstruction region. Namely, since back projection is not carried out in the entire region, it is possible to obtain two-dimensional absorption coefficient pictorial images in a short time.

At the step ST27, the image reconstruction section 44 converts values of respective pixels of absorption coefficient pictorial images formed in the reconstruction region to CT number values. Thus, the image reconstruction section 44 forms a single or plural two-dimensional pictorial image data (images of layered surfaces in the body axis direction). This two-dimensional image data is displayed on the display monitor 46. Thus, an operator observes a pictorial image displayed to judge whether collected luminance data is good or bad. Namely, similarly to the case where an approach is employed to obtain an image of a layered surface perpendicular to the body axis described above, without executing back projection in the entire region, it is possible to carry out in a short time, judgment as to whether luminance data is good or bad. It is to be noted that the above-described processing may be carried out by the CPU 43 in place of using the image reconstruction section 44.

The image processing section 45 implements image processing such as extraction of contour, etc. to three-dimensional pictorial image data as occasion demands to deliver it to the display monitor 46. The display monitor 46 displays a three-dimensional pictorial image based on three-dimensional pictorial image data or three-dimensional pictorial image data to which image processing such as extraction of contour, etc. is implemented. Further, the display monitor 46 displays a two-dimensional image based on two-dimensional image data in a body axis direction or in a direction perpendicular to the body axis delivered from the image processing section 45 as occasion demands. Namely, while the conventional system required 640 seconds for obtaining images of 128 layered surfaces as described above, this radiation diagnostic system can obtain images of many layered surfaces corresponding to resolution in a horizontal or vertical direction of the CCD camera 23 for a time period during which the X-ray vessel 13 is caused to make half turn or one revolution. In other words, this radiation diagnostic system can obtain, in a short time, three-dimensional pictorial images having high resolution. Accordingly, this radiation diagnostic system is suitable for practical use as a clinical equipment for patients, and is permitted to reduce a quantity of exposure of X-ray to much more degree as compared to the conventional equipment. Further, the X-ray/light conversion element 21 is caused to be in a flat form such that it has a relatively large area as described above, thereby making it possible to obtain a three-dimensional image having less distortion in a broad range. In addition, since this radiation diagnostic system does not use the X-ray image intensifier as described above, this system is not affected by vibration or geomagnetism.

The operation of the above-described drive unit 30 will now be described.

In this radiation diagnostic system, a video signal from the CCD camera 23 is directly delivered, viz., in the same use state as in the X-ray television system described in the prior art. Thus, an operator observes an image displayed on the display monitor, thereby making it possible to move the subject 50 so that an interest region or focus is located substantially at the central portion of the screen, or to vary so called a magnification in dependency upon the size of the subject 50.

In actual terms, the display monitor 46 is adapted to include a write pen capable of designating position or region of a picture on screen. For example, when an operator designates (marks) an interest portion of a picture of the display monitor 46 by using a write pen, the controller 39 determines a quantity of movement required so that the marked position is located substantially at the central portion of the picture, on the basis of position information indicating the marked position from the display monitor 46 to deliver a control signal indicating that quantity of movement to the bed drive section 36. The bed drive section 36 drives the bed 35 in the body axis direction of the subject 50 on the basis of the control signal. Thereafter, as described above, a three-dimensional pictorial image is formed on the basis of two-dimensional pictorial images in plural directions, whereby a three-dimensional image of the interest region or focus is displayed so that it is located substantially at the central portion of the screen. It is to be noted that as a pointing device for pointing or marking position of a picture on screen, a mouse, a joy stick, or a tablet etc. may be used in addition to the above-described write pen.

Further, since the magnification is based on ratio between the distance between the X-ray vessel 13 and the subject 50 and the distance between the X-ray vessel 13 and the X-ray/light conversion element 21, the controller 39 determines a distance between the X-ray vessel 13 and the X-ray/light conversion element 21 where the image of the subject 50 displayed has a desired size (dimension), e.g., occupies more than 75% of a picture on screen, on the basis of profile (contour) information of the image of the subject 50 displayed on the screen from the display monitor 46, thus to deliver a control signal indicating that distance to the vessel drive section 33. The vessel drive section 33 drives the X-ray vessel 13 on the basis of the control signal. At this time, the controller 39 determines an optimum focal size in dependency upon the distance between the X-ray vessel 13 and the X-ray/light conversion element 21 to deliver a control signal for selecting a focal size to the focal size switcher 34. The focal size switcher 34 switches the focal size of the X-ray vessel 13 on the basis of the control signal. Thereafter, as described above, a three-dimensional pictorial image is formed on the basis of two-dimensional images from plural directions, whereby the three-dimensional image of the subject 50 is displayed on the display monitor 46 in a desired size, e.g., in such a manner that it takes more than 75% of the screen. In other words, the X-ray can be effectively used, and the resolution can be enhanced.

Meanwhile, the means for adjusting the size of a display picture may be adapted not only to vary the above-described distance between the X-ray vessel 13 and the X-ray/light conversion element 21, but also to move the CCD camera 23 in the optical axis direction of a visible light reflected by the mirror 22 as shown in the above-mentioned FIG. 1, for example. In actual terms, the controller 39 determines the position of the CCD camera 23 where the size of an image of the subject 50 displayed occupies, e.g., more than 75% of the so-called picture angle of the CCD camera 23, on the basis of profile information of the image of the subject 50 displayed on the screen from the display monitor 46 to deliver a control signal indicating that position to the camera position drive section 38. The camera position drive section 38 moves the camera mount 37 in the optical axis direction of a visible light on the basis of the control signal. As a result a three-dimensional pictorial image of the subject 50 is displayed on the display monitor 46 so that it occupies more than 75% of the screen, and similar effects described above can be provided. In addition, e.g., CCD camera 23 may be caused to be a video camera provided with a zoom lens, thus to control zooming by the controller 39.

As is clear from the foregoing description, the radiation diagnostic system according to this invention irradiates radioactive rays, e.g. X-rays to the subject to detect the intensity distribution of the X-rays transmitted through the subject and allows the radiation output means and the two-dimensional radiation detection means which are caused to be in one body to turn round the subject to form a three-dimensional pictorial image on the basis of the intensity distribution of radioactive rays in plural directions, thereby making it possible to obtain a three-dimensional pictorial image having high resolution in a short time. In other words, this radiation diagnostic system is suitable for practical use as a clinical equipment for patients, and is permitted to reduce the quantity of exposure of X-ray to much more degree as compared to the conventional system. In addition, the X-ray/light conversion element is permitted to be in a flat form such that it has a relatively large area. Thus, it is possible to obtain a three-dimensional pictorial image having less distortion in a broad region.

Moreover, the X-ray/light conversion element is caused to be a fluorescent substance including rare earth element thereby making it possible to block or impede X-rays transmitted through the fluorescent substance. This can prevent in advance trouble of the CCD camera.

Further, the distance between the radiation output means and the two-dimensional radiation detecting means is varied, and the focal size is switched at this time in dependency upon the distance between the radiation output means and the two-dimensional radiation detecting means, thereby making it possible to obtain a three-dimensional image of a desired size. In other words, the X-ray can be effectively utilized and the resolution can be enhanced.

Further, a CCD camera provided with, e.g., a zoom lens, a CCD camera movable in an optical axis direction, or the like is used as the two-dimensional radiation detecting means, thereby making it possible to adjust a picture angle of the two-dimensional radiation detecting means, thus to obtain a three-dimensional image of a desired size.

Further, this radiation diagnostic system comprises a bed for mounting a patient as a subject thereon, bed drive means for moving the bed in the body axis direction of the patient display means for displaying a pictorial image based on the intensity distribution of radioactive rays from the two-dimensional radiation output means, and control means for controlling the bed drive means to control the bed drive means so that an interest region is located substantially at the central portion of a screen of the display means, by the control means on the basis of a profile of an image of the subject displayed on the display means, thereby making it possible to display a three-dimensional image of the interest region or focus so that it is located substantially at the central portion of the screen.

In addition, an approach is employed to form a two-dimensional image in a body axis direction or in a direction perpendicular to the body axis direction of a patient as the subject prior to forming a three-dimensional image by the convolution back projection method, thereby making it possible to judge in advance whether or not the intensity distribution of radioactive rays in plural directions detected by the two-dimensional radiation detecting means is valid.

What is claimed is:

1. A radiation diagnostic system comprising:
   radiation output means for outputting radioactive rays at a fan angle;
   two-dimensional radiation detecting means disposed at a position opposite to said radiation output means through a subject, having a plane shape and adapted to detect intensity distribution of radioactive rays transmitted through said subject;
   rotation drive means for allowing said radiation output means and said two-dimensional radiation detecting means which are integrated in one body to turn round said subject;
   information processing means for forming a three-dimensional pictorial image on the basis of the intensity distribution of radioactive rays in plural directions from said two-dimensional radiation detecting means;
   said radiation output means outputting radioactive rays for each predetermined angle of rotation while turning round said subject, and said information processing means forming the three-dimensional pictorial image from a two-dimensional pictorial image as the intensity distribution of radioactive rays in plural directions from said two-dimensional radiation detecting means; and
   drive means for allowing the distance between said radiation output means and said two-dimensional radiation detecting means to be adjustable.

2. A radiation diagnostic system as set forth in claim 1, which further comprises:
   display means for displaying a pictorial image based on the intensity distribution of radioactive rays from said two-dimensional radiation detecting means; and
   control means for determining a distance between said radiation output means and said two-dimensional radiation detecting means such that the ratio of an image of the subject occupied on the screen takes a value more than a predetermined value, on the basis of a profile of the image of the subject displayed on the display means, and for controlling said drive means so that said distance is provided.

3. A radiation diagnostic system as set forth in claim 1,
   wherein said radiation output means is comprised of an X-ray source having at least two focal sizes,
   said system further including switching means for switching and selecting the focal size in dependency upon the distance between said radiation output means and said two-dimensional radiation detecting means.

4. A radiation diagnostic system comprising:
   radiation output means for outputting radioactive rays at a fan angle;
   two-dimensional radiation detecting means disposed at a position opposite to said radiation output means through a subject having a plane shape and adapted to detect intensity distribution of radioactive rays transmitted through said subject;
   rotation drive means for allowing said radiation output means and said two-dimensional radiation detecting means which are integrated in one body to turn round said subject;
   information processing means for forming a three-dimensional pictorial image on the basis of the intensity distribution of radioactive rays in plural directions from said two-dimensional radiation detecting means;
   said radiation output means outputting radioactive rays for each predetermined angle of rotation while turning round said subject and said information processing means forming the three-dimensional pictorial image from a two-dimensional pictorial image as the intensity distribution of radioactive rays in plural directions from said two-dimensional radiation detecting means; and
   said two-dimensional radiation detecting means including picture angle adjustment means for adjusting a picture angle.

5. A radiation diagnostic system as set forth in claim 4, wherein said radiation output means is comprised of an X-ray source; and said two-dimensional radiation detecting means is composed of an X-ray/light conversion element for converting an X-ray to a visible light and a CCD camera provided with a zoom lens as said picture angle adjustment means.

6. A radiation diagnostic system as set forth in claim 4, wherein said radiation output means is comprised of an X-ray source, and said two-dimensional radiation detection means is composed of an X-ray/light conversion element for converting X-rays to a visible light and a CCD camera, said system including, as said picture adjustment means, moving means for moving said CCD camera in an optical axis direction thereof.

7. A radiation diagnostic system comprising:

radiation output means for outputting radioactive rays at a fan angle, said radiation output means is comprised of an X-ray source having at least two focal sizes;

two-dimensional radiation detecting means disposed at a position opposite to said radiation output means through a subject said detection means having a plane shape for covering an entire thorax of a patient as the subject and adapted to detect intensity distribution of radioactive rays transmitted through said subject said two-dimensional radiation detection means being composed of an x-ray/light conversion element for converting X-rays to a visible light and a CCD camera, said X-ray/light conversion element being comprised of a fluorescent substance including a rare earth element said CCD camera provided with a zoom lens;

switching means for switching and selecting the focal size in dependency upon the distance between said radiation output means and said two-dimensional radiation detecting means;

rotation drive means for allowing said radiation output means and said two-dimensional radiation detecting means which are integrated in one body to turn round said subject;

information processing means for forming a three-dimensional pictorial image on the basis of the intensity distribution of radioactive rays in plural directions from said two-dimensional radiation detecting means, said information processing means forms a three-dimensional pictorial image by the convolution back projection method;

said intensity distribution of radioactive rays outputted from said radiation output means having irregularity such that the intensity is high in a central portion thereof and low in peripheral portions thereof, said radiation diagnostic system having correction means for correcting said irregularity;

drive means for allowing the distance between said radiation output means and said two-dimensional radiation detecting means to be adjustable;

display means for displaying a pictorial image based on the intensity distribution of radioactive rays from said two-dimensional radiation detecting means;

control means for determining a distance between said radiation output means and said two-dimensional radiation detecting means such that the ratio of an image of the subject occupied on the screen takes a value more than a predetermined value on the basis of a profile of the image of the subject displayed on the display means, and for controlling said drive means so that said distance is provided;

a bed for mounting a patient as the subject thereon;

bed drive means for moving said bed in a body axis direction of the patient; and second control means for controlling said bed drive means so that an interest region is located substantially at the central portion of the screen of said display means.

* * * * *